US008053238B2

(12) United States Patent
Jin et al.

(10) Patent No.: US 8,053,238 B2
(45) Date of Patent: *Nov. 8, 2011

(54) ISOLATED POPULATION OF PLANT SINGLE CELLS AND METHOD OF PREPARING THE SAME

(75) Inventors: Young Woo Jin, Jeonju (KR); Eun Kyong Lee, Iksan (KR)

(73) Assignee: Unhwa Corporation, Jeonju, Jeollabuk-do (KR)

(*) Notice: Subject to any disclaimer, the term of this patent is extended or adjusted under 35 U.S.C. 154(b) by 0 days.

This patent is subject to a terminal disclaimer.

(21) Appl. No.: 12/117,783

(22) Filed: May 9, 2008

(65) Prior Publication Data

US 2009/0011477 A1    Jan. 8, 2009

Related U.S. Application Data

(63) Continuation-in-part of application No. 12/063,929, filed on Feb. 15, 2008, now Pat. No. 8,017,397, which is a continuation-in-part of application No. PCT/KR2006/001544, filed on Apr. 25, 2006.

(30) Foreign Application Priority Data

Oct. 31, 2005  (KR) .................. 10-2005-0103445

(51) Int. Cl.
  *C12N 5/00*   (2006.01)
  *C12N 5/02*   (2006.01)
(52) U.S. Cl. ..................... 435/422; 435/410
(58) Field of Classification Search ........... 435/410, 435/123, 422
See application file for complete search history.

(56) References Cited

U.S. PATENT DOCUMENTS

| 5,019,504 | A | * | 5/1991 | Christen et al. | ........... 435/123 |
| 5,344,775 | A | | 9/1994 | Smith | |
| 5,407,816 | A | * | 4/1995 | Bringi et al. | ........... 435/123 |
| 2008/0194025 | A1 | | 8/2008 | Jin | |
| 2010/0233813 | A1 | | 9/2010 | Jang et al. | |
| 2010/0255585 | A1 | | 10/2010 | Yu et al. | |
| 2010/0272692 | A1 | | 10/2010 | Park et al. | |
| 2011/0033903 | A1 | | 2/2011 | Jin | |
| 2011/0039312 | A1 | | 2/2011 | Jin | |

FOREIGN PATENT DOCUMENTS

| EP | 1538214 A1 | 6/2005 |
| KR | 1997-0009157 B1 | 6/1997 |
| KR | 10-0290004 B1 | 5/2001 |
| KR | 2001-0094111 A | 10/2001 |
| KR | 2003-0063724 A | 7/2003 |
| KR | 2004-0108052 | 12/2004 |
| WO | WO 93/17121 A1 | 9/1993 |
| WO | 2007/052876 A1 | 5/2007 |
| WO | 2009/048306 A1 | 4/2009 |
| WO | WO 2009/139581 A2 | 11/2009 |
| WO | WO 2009/151302 A2 | 12/2009 |
| WO | WO 2010/019016 A2 | 2/2010 |
| WO | WO 2010/038991 A2 | 4/2010 |
| WO | WO 2010/095911 A2 | 8/2010 |

OTHER PUBLICATIONS

Naill et al. "Preparation of Single Cells from Aggregated *Taxus* Suspension Cultures for Population Analysis," Biotechnology and Bioengineering, vol. 86, No. 7, Jun. 30, 2004, pp. 817-826.*
Roberts et al. "A simple method for enhancing paclitaxel release from *Taxus canadensis* cell suspension cultures utilizing cell wall digesting enzymes," Plant Cell Rep (2003) 21:1217-1220.*
Pyo et al. "Efficient purification and morphology characterization of paclitaxel from cell cultures of *Taxus chinensis*," Journal of Chemical and Technology and Biotechnology, (2004), 79: 1162-1168.*
Ziv, Meira "Bioreactor Technology for Plant Micropropagation," Horticultural Reviews, vol. 24, (2000), pp. 1-30.*
Esau, Katherine "Anatomy of Seed Plants," Second Edition, John Wiley & Sons, Inc., (1977), p. 30.*
Ye, Zheng-Hua "Vascular Tissue Differentiation and Pattern Formulation in Plants," Annu. Rev. Plant Biol., (2002), 53:183-202.*
Roberts et al. "A simple method for enhancing paclitaxel release from *Taxus canadensis* cell suspension cultures utilizing cell wall digesting enzymes," Plant Cell Rep (2003) 21:1217-1220.*
Biotechnology Letters "Culture of isolated single cells from *Taxus* suspensions for the propagation of superior cell populations" ; Naill M.C., et al.; 2005; p. 1725-1730.
Biotechnology and Bioengineering; "Preparation of Single Cells From Aggregated *Taxus* Suspension Cultures for Population Analysis", Naill M.C.; et al., 2004; p. 817-826.
Plant Cell Reports "Initiation and growth of cell lines of *Taxus brevifolia* (Pacific yew);" D.M. Gibson, et al.; 1993; p. 479-482.
Journal of Bioscience and Bioengineering; "Plant Cell Culture for Production of Paclitaxel and Other Taxanes" ; Zhong, J.; 2002, p. 591-599.
Biotechnol. Prog., "Flow Cytometric Identification of Paclitaxel-Accumulating Subpopulations"; Naill, M.C., et al., 2005; p. 978-983.
Kumar et al. "Morphogenetic responses of cultured cells of cambial origin of a mature tree-Dalbergia Sissoo-Roxb.," Plant Cell Reports (1991) 9:703-706.
Dodds et al. "Experiments in Plant Tissue Culture," Cambridge University Press, 3rd Edition; reprinted in 1999; pp. 92-95.
White, P.R., "Potentially unlimited growth of excised plant callus in an artificial nutrient," American Journal of Botany, vol. 26(2), 1939, pp. 59-64.
Baebler, S., et al., "Establishment of cell suspension cultures of Yew (*Taxus x Media* Rehd.) and assessment of their genomic stability," *In Vitro Cell. Dev. Biol. Plant* 41:338-43, Society for In Vitro Biology, United States (May-Jun. 2005).

(Continued)

*Primary Examiner* — Susan B McCormick Ewoldt
(74) *Attorney, Agent, or Firm* — Sterne, Kessler, Goldstein & Fox P.L.L.C.

(57) ABSTRACT

This invention is a method of minimizing the variation of cell growth and production through homogeneous cell line development. To be more specific, it is the method of isolating and proliferating single cell clone from the procambium to promote the stability of the plant-derived biologically active substances production by solving the problems of decrease in cell growth and the productivity during the long term culture.

8 Claims, 5 Drawing Sheets

OTHER PUBLICATIONS

Bai, J., et al., "Production of Biologically Active Taxoids by a Callus Culture of *Taxuscuspidata*," *J. Nat. Prod.* 67(1):58-63, American Chemical Society and American Society of Pharmacognosy, United States (Jan. 2004; Epub Dec. 3, 2003).

Ben Jouira, H., et al., "Adventitious shoot production from strips of stem in the Dutch elm hybrid 'Commelin': plantlet regeneration and Neomycin sensitivity," *Plant Cell, Tissue and Organ Culture* 53:153-160, Kluwer Academic Publishers, Netherlands (1998).

Frankenstein, C., et al., "The onset of Cambium activity—A matter of agreement?" *Dendrochronologia* 23:57-62. Elsevier GmbH, Italy (2005).

Freeman, S., *Biological Science,* Second Edition, p. 823, Pearson Education, Inc., United States (2005).

Hirasuna, T.J., et al., "Taxol production in suspension cultures of *Taxusbaccata*," *Plant Cell, tissue and Organ Culture* 44(2):95-102, Kluwer Academic Publishers, Netherlands (1996).

Kim, M.H., et al., "Growth Promotion of *Taxusbrevifolia*Cell Suspension Culture using Conditioned Medium," *Biotechnol. Bioprocess Eng.* 5:350-4, Korean Society for Biotechnology and Bioengineering, Korea (2000).

Lee, E.K., et al., "Cultured cambial meristematic cells as a source of plant natural products," *Nat. Biotechnol.* 28(11):1213-7, Nature America Publishing, United States (Nov. 2010, Epub Oct. 24, 2010).

Reynolds, L.B., "Effects of Harvest Date on Some Chemical and Physical Characteristics of American Ginseng (*Panaxquinquefolius* L.)," *J. Herbs, Spices & Medicinal Plants* 6(2):63-69, The Haworth Press Inc., United States (1998).

Roberts, S. and Kolewe, M., "Plant natural products from cultured multipotent cells," *Nature Biotechnol.* 28(11):1175-6, Nature America Publishing, United States (Nov. 2010).

Strobel, G.A., et al., "Taxol formation in yew —*Taxus*," Plant Sci. 92:1-12, Elsevier Scientific Publishers Ireland Ltd., Ireland (1993).

Wang, C., et al., "Enhanced TaxolProduction and Release in *Taxuschinensis*Cell Suspension Cultures with Selected Organic Solvents and Sucrose Feeding," *Biotechnol. Prog.* 17(1):89-94, American Chemical Society and American Institute of Chemical Engineers, United States (Jan.-Feb. 2001; Epub Dec. 2, 2000).

Wang, C., et al., "Enhancement of Taxol production and excretion in *Taxuschinensis* cell culture by fungal elicitation and medium renewal," *Appl. Microbiol. Biotechnol.* 55(4):404-10, Springer International, Germany (May 2001; Epub Mar. 6, 2001).

Wickremesinhe, E.R.M. and ARTECA, R.N., "*Taxus*CEll Suspension Cultures: Optimizing Growth and Production if Taxol," *J. Plant Physiol.* 144:183-3, Gustav Fischer Verlag, Germany (1994).

Wu, J. and Lin, L., "Enhancement of taxol production and release in *Taxuschinensis* cell cultures by ultrasound, methyl jasmonate and in situ solvent extraction," *Appl. Microbiol. Biotechnol.* 62(2-3):151-5, Springer Verlag, Germany (Aug. 2003;Epub Mar. 13, 2003.)

Yokoi, H., et al., "High Density Cultivation of Plant Cells in a New Aeration-Agitation Type Fermentor,MaxblendFermentort®," *Journal of Fermentation and Bioengineering* 75(1):48-52, Society for Biotechnology, Japan (1993).

Yukimune, Y., et al., "Methyl jasmonate-induced overproduction of paclitaxel and baccatin III in *Taxus* cell suspension cultures," *Nat. Biotechnol.* 14(9):1129-32, Nature America Publishing, United States (Sep. 1996).

Zhang, C.H., et al., "Enhanced paclitaxel production induced by the combination of elicitors in cell suspension cultures of *Taxuschinensis*," *Biotechnol. Lett.* 22:1561-4, Kluwer Academic Publishers, Netherlands (2000).

English language Abstract of Korean Patent Publication No. KR1997-0009157 B1, European Patent Office, espacenet database—Worldwide, (1997).

English language Abstract of Korean Patent Publication NO. KR2001-0094111 A, European Patent Office, esoacenet database—Worldwide, (2001).

English language Abstract of Korean Patent Publication No. KR100290004 B1, European Patent Office, espacenet database—Worldwide, (2001).

English language Abstract of WIPO European Patent Publication No. WO 2009/139581 A2, European Pantent Office, espacenet database—Worldwide, (2009).

English language Abstract of WIPO Patent Publication No. WO 2009/151302 A2, European Patent Office, espacenet database—Worldwide, (2009).

English language Abstract of WIPO Patent Publication No. WO 2010/019016 A2, European Patent Office, espacenet database—Worldwide, (2010).

English language Abstract of WIPO Patent Publication No. WO 2010/038991 A2, European Patent Office, espacenet database—Worldwide, (2010).

English language Abstract of WIPO Patent Publication No. WO 2010/095911 A2, European Patent Office, espacenet database—Worldwide, (2010).

\* cited by examiner

ISOLATED POPULATION OF PLANT SINGLE CELLS AND METHOD OF PREPARING THE SAME

CROSS-REFERENCE TO RELATED APPLICATIONS

This application is a continuation-in-part of U.S. patent application Ser. No. 12/063,929 filed in the U.S. Patent & Trademark Office on Feb. 15, 2008 entitled "Stability of Secondary Metabolite Mass Production Through Synchronized Plant Cell Cultures" in the name of Young Woo Jin, which was filed under the provisions of 35 U.S.C. §371 and claims the priority of International Patent Application No. PCT/KR2006/001544 filed on 25 Apr. 2006, which claims priority to Korean Patent Application No. 10-2005-0103445 filed on 31 Oct. 2005, which are all hereby incorporated by reference in their entirety.

TECHNICAL FIELD

Plant has been used very importantly not only as our food supply but also as the source of extensive chemical substances including, pharmaceuticals, fragrances, colors, agricultural chemicals and dyes etc. Biologically active compounds that are produced from plants are mostly secondary metabolites. There is a greater interest on the secondary metabolites, such as alkaloid, allergen, amino acid, anthraquinone, antileukaemic agent, antimicrobial agent, antitumor agent, antiviral agent, enzyme, flavonoids, insecticide, opiate, perfume, pigment, vitamin, and polysaccride etc., because most of them work as physiologically active substances. According to Zhong (2002), there are about 100,000 known plant secondary metabolites and more than 25% of the medicine that are practically used is plant-derived substances. Every year, novel secondary metabolites are discovered continually.

In the method of obtaining these metabolites, there are many problems such as difficult chemical synthesis in spite of the recent astonishing developments of the organic chemistry, demolition of the nature due to exploitation and environmental pollution and changes of the content of metabolites and increase of the production cost depending on the culture conditions, like season, region and climate. Therefore, there are on going active attempts to produce secondary metabolites through in vitro culture technique which has advantages of controlling the adequate external environmental conditions and producing on a large scale even in a small space.

BACKGROUND ART

According to KR patent 0130100, production of biologically active substances through plant cell culture has more advantages than direct extraction from the plant. Plant cell culture is considered as an optimal method for continual production which is not influenced by environment and for solving the pending problems like destruction of ecology.

Nail & Roberts (2004), however, indicated slow growth rate and low productivity of the plant cell culture for the secondary metabolite production. To solve this problem, there are studies of the optimization of the media, culture conditions, process and elicitation for higher productivity etc. (Zhong 2002). In the International patent WO93/17121, various media was used to culture diverse *Taxus* for the increase in cell growth rate and paclitaxel productivity. Based on the results of the experiments, elicitation conditions for paclitaxel mass production was indicated. Despite the improvements to the production of valuable secondary metabolites, variability is still a major issue for the production of paclitaxel from *Taxus* and other valuable substances from numerous plant systems.

Production of secondary metabolites through large scale plant cell culture is commercially possible only when there is a stable maintenance of rapid cell growth and high metabolite production during long term culture. The ability of the cell lines that could produce distinct metabolites are not stable which cause the cell lines to lose their initial productivity through subcultures; it is not too much to say that success and failure are depended on how we overcome these problems.

In plant cell culture, although the cells are derived from one plant, metabolite productivity of each cell line is different and unstable. Therefore, establishing the cell lines that have high productivity and genetic stability is most important than anything else.

Cell Lines Derived from Single Cells & and Multiple Cells

Plant cell lines derived from single cells have lower variability than the cell lines derived from multiple cells; this results in higher productivity. In preceding inventions, stem, root, seed, needle and leaf were used as the best explants for cell line induction. These stem, root, seed, needle and leaf are tissues that are composed of the cells with distinct functions and morphology. Callus, cell lines derived from these tissues is not of one kind. Therefore, there are limitations on the attempts to reduce the productivity variation of the callus derived from the tissues consisted of multiple cells.

Cell Aggregation

One of the distinguishing characteristics of plant cell culture is cell aggregation. According to the patent 0364478, diameter of the plant cell is 30-300 µm which is about 30 times bigger than the animal cell. Because plant cell walls have natural tendency to adhere together, it is not possible to obtain suspension which consists only of dispersed single cells. The proportion and the size of cell aggregates vary according to plant variety and the medium in which the culture is grown. Nail & Roberts indicated that cell aggregation leads to a difference in local environment between interior and exterior of the cells, which can result in culture heterogeneity and ultimately leads to changes in growth and metabolism.

The purpose of suspension culture is to obtain pure single cells. To accomplish this objective, filtration, maceration and protoplast culture by using enzyme were used. However, filtration and maceration do not provide complete pure single cells. Protoplast culture technique which eliminates the cell wall is the most reliable method for generating single cells, but the enzyme used for the protoplast culture cause cell wall damages or breakages that result in the change of cell physiology. Moreover, hydrophobic secondary metabolites such as paclitaxel can be stored in the cell wall, so the changes in the cell wall have profound relationship with productivity.

Also, cell aggregation has long been a major obstacle to the accurate measurement of cell growth by number and to biochemical assays to individual cells. According to Nail & Roberts (2004), if single cell culture is possible, it will readily provide faster information about the behavior of cell units in the culture such as biosynthesis, storage, and degradation etc. of secondary metabolites.

Dedifferentiation

The dedifferentiated cell line, which is callus, shows great variability in the production of secondary metabolites due to somaclonal variation. Callus derived from the permanent tissues such as leaves, stem, root and seed that are composed of the cells with distinct functions and morphology usually show dramatical changes even on slightly different microenvironments because it is a secondary meristem formed by dedifferentiation. Due to this sensitivity, Hirasuna et al. (1996) investigated to identify the cell culture conditions, especially initial cell density, subculture interval and temperature, and to maintain them as precisely as possible.

Scale Up

In order to produce secondary metabolites through plant cell culture for commercialization, scale up is essential. Bioreactor has been applied for mass production after many patents and articles were published, reporting about successful production of metabolites through cell culture in a laboratory scale. According to patent 0290004, application of bioreactor for mass production provides very different culture environment from the flask in a laboratory scale which results in the decrease in growth rate and productivity and change in the metabolites. When the bioreactor is applied for mass production, changes in growth rate, productivity and metabolites have become problems in commercialization of biologically active substances through cell culture. In the scale up of plant cell cultures, bioreactor which receives the air through exterior power or the bioreactor with impeller by considering the efficiency of the mixing and aeration are preferred. However, cell viability decreases abruptly in the bioreactor because plant cells are weak for shear. Therefore, a method to reduce shear is necessary. The cause of the shear sensitivity of the plant cell is explained by its large size, rigid cell wall, aggregation and extensive vacuolate (Yokoi, et al, 1993). To solve these problems in the bioreactor, a low shear generating bioreactor was investigated in the past by controlling its agitating speed and modifying the impeller type. However, it still bears negative results because the cell lines could not overcome the differences of the microenvironment.

Cryopreservation

Cryopreservation allows the long term cell maintenance by ceasing most of the metabolism of the cells in the extremely low temperature. It signifies the recovery of the cells without genetic, characteristics and biosynthetic variation after cryopreservation. By using cryopreservation, lost of the cells from contaminations could be eliminated and the genetic variation in the continuous cell lines could be minimized. In cGMP, the preservation of the cell lines for a long period is mandatory for the stable supply of raw materials. Usually, cultured animal cells could undergo cryopreservation for many years, but the similar cryopreservation technique is much more challenging for cultured plant cells. Cultured plant cells are heterogeneous and show diversity in physiology and morphology. Therefore, plant suspension cells require many processes for cryopreservation and inadequate cryopreservation could cause variability.

Conditioning Factors

Kim et al. (2000) demonstrated that cell division can be stimulated if some media from actively dividing cultures was added to the cultures that lost cell division ability. In the production of anthocyanin through rose suspension culture, the productivity increased when some media of strawberry suspension culture was added to the rose suspension culture. In this way, the factors that were produced and secreted from the cultured cells to stimulate the cell growth or the production of the secondary metabolites are called conditioning factors. Yet, these conditioning factors have not been identified concretely and there are only some understanding of conditioning factors acting as chemical signals for the cell growth and metabolite production. Also, there are few reports on the potent substances, such as phosphates and calmodium which could be considered as conditioning factors. Conditioning factors can be supplied through conditioned media or helper cells.

Perfusion Cultivation

Among the cell culture methods, there is a batch cultivation involving the inoculation of the cell and the media together in the beginning and no further nutrition supplementation. Also, there is a continuous cultivation, involving the supplementation of the new media as the spent media that contains metabolites is retrieved simultaneously at a consistent speed during the culture period for the prevention of nutrition depletion.

Batch cultivation is difficult in the commercial level due to its low productivity. Among the continuous culture methods, perfusion cultivation is receiving much attention these days. In perfusion culture, the cells are remained in the bioreactor, and new media is supplied as the spent media that contains metabolites is retrieved.

According to Zhang et al. (2000), elicitation is one of the most effective ways to promote the secondary metabolites production in cell culture. Elicitation encourages secondary metabolite synthesis, but it induces cell growth inhibition and the rapid decrease in the cell viability. Hence, secondary metabolite synthesis by elicitation could be maintained only for a short period and it is very limited. As Wang et al. (2001) presented, perfusion cultivation is a strategy to minimize these negative effects by elicitation and to maximize the productivity.

Wang et al. (2001) and Wu & Lin (2003) reported as follows. Secondary metabolites that are produced by elicitation are stored inside of the cell (vacuole or cell wall) or released outside of the cell (media). During the process of culture, releasing secondary metabolites from the cell and removing it from the media could bring easier purification and could diminish the feedback inhibition of biosynthesis and degradation and conversion of the products. Therefore, by retrieving the spent media and supplying with a new media, secretion of internal and external metabolites could extend the viability and biosynthesis of the cells. And it could remarkably increase the productivity.

Storage and the secretion of secondary metabolites showed great differences depending on the cell lines. *Taxus media* cell line (Wickremesinhe and Arteca 1994) did not excrete any. Consequently, establishing the cell line that has outstanding secretion ability is required.

Cambium Culture

Cambium is a lateral meristem that is located on the lateral side of the plant. In the gymnosperm and woody dicotyledon plants, there is a hypertrophic growth due to the continual activity of the cambium; as a result, giant plants having more than 11,000 years of the growth rings exist. In genetics, meristems could be classified as primary and secondary meristem. Primary meristem represents the meristem that forms during embryogenesis and participates in the plant growth after seed germination. Secondary meristem represents the meristem that is formed by dedifferentiation of the plant permanent tissue. Cambium is a primary meristem with meristematic continuity derived from the procambium without the intervene of the permanent tissue.

Growth of this primary meristem is indeterminate and could be continued if the conditions are given. Therefore, cambium culture has been used for rapid mass propagation of the cells.

In the preceding studies, cambium explants were prepared as follows: after the bark was peeled off, two longitudinal cuts, approximately 1 mm deep in order to reach the xylem, were made into the woody stem at an interval of 5 mm. They called these explants 'cambium', which was constituted of part of the phloem, cambium and a small chip of xylem (Jouira et al., 1998).

It is reasonable to say that cells which are induced by the method as mentioned above are not the sole origin of cambium, but of multiple tissues, which can be solemnly distinguished anatomically such as phloem, cambium and xylem. Thus, we could indicate that the method mentioned above is not the ideal technique to separate only the cambium elaborately from the various tissues that constitute the stems. A creative method to separate only the cambium or procambium from the various tissues of stems has been in demand.

DISCLOSURE

Technical Problem

The objective of this invention is to generate the method to produce single cell clone by separating and culturing only the procambium from the twig. To put it concretely, the goal of this invention is to solve the variation in plant cell culture and to generate stable production method for plant biologically active substances by separating the procambium purely through combining the methods of cell and physiological chemistry separation to the preceding physical separation method that utilizes the scalpel.

Another purpose of this invention is to generate stable cell proliferation by separating and culturing only the procambium from the *Taxus* twig and to generate the method of paclitaxel production.

Technical Solution

To achieve the above objectives, in one aspect, the present invention provides a method for isolating plant procambium-derived single cell clone, the method following: (a) preparing and then sterilizing the plant tissue; (b) collecting the tissue containing procambium from the said sterilized plant tissue; (c) culturing the said tissue containing procambium, and thereby inducing a procambium layer which is proliferated from procambium, and a callus layer which is derived from regions except procambium and proliferated in an irregular form; and (d) collecting the single cell clone by isolating the said procambium layer from the said callus layer.

Preferably, the step (c) comprises culturing the said tissue in medium containing auxin. And in a preferred embodiment, the medium contains 1~3 mg/L of the auxin.

In another aspect, the present invention provides a single cell clone induced from plant procambium, the single cell clone has the following characteristics: (a) above 90% cells in suspension culture exist as single cells; (b) having multiple vacuoles morphologically; (c) growing faster than the cell line derived from regions except procambium of the same plant origin, and culturing stably for a long time; (d) having low sensitivity to shear stress in the bioreactor; and (e) being innately undifferentiated.

Preferably, the plant is the genus *Taxus*. And in a preferred embodiment, the genus *Taxus* procambium-derived single cell clone has an ability of releasing 404~1077 times more paclitaxel than the cell lines derived from regions except procambium of the same plant origin.

In still another aspect, the present invention provides a method for producing plant-derived biologically active substances, the method comprising the steps of: (a) producing the active substances by culturing the above single cell clone; and (b) collecting said active substances. Preferably culturing of the step (a) comprises retrieving the media used in culturing of said single cell clone culture and then supplying with a new media.

In a preferred embodiment, the single cell clone is the genus *Taxus* procambium-derived single cell clone, and the compound is paclitaxel. In this case, the media may further contain one or more materials selected from the group consisting of methyl jasmonate, phenylalanine and chitosan.

And, the present invention provides a method for preserving a plant cell line, the method comprises cryoperservating single cell clone derived from plant procambium, which are isolated by the above method.

Advantageous Effects

According to the methods of this invention, it is possible to culture single cell clone that has the meristematic continuity of primary meristem without going through dedifferentiation by precisely separating only the procambium from various tissues of woody plant twig or stem. Cell line of this invention allows stable production of biologically active substances due to less change in the cell growth rate and growth pattern during the long term culture. It is also optimal for the mass production in commercial level because it is less sensitive to shear in the bioreactor compared to the cell lines derived from the preceding techniques due to less aggregation and multiple vacuoles.

Metabolite activation can be stimulated by supplementing conditioning factors to this cell line and cell vitality and biosynthesis can be extended as the cells releasing considerable amount of production into the extracellular media through perfusion culture. High recovering rate after cryopreservation due to homogeneity and division ability of this cell line devises the establishment of cell bank. Through this invention, close relationship between homogeneity of the cultures and variation of secondary metabolites are confirmed, and the method of this invention could develop the strategy for commercialization as it controls and reduces the variability of diverse biologically active substance production.

MODES OF THE INVENTION

Practical examples of the invention are explained below. Induction and proliferation method of single cell clone from the procambium is not only utilized in paclitaxel production system but it may also be utilized in all plant secondary metabolite production system. The following examples are offered by way of illustration, not by way of limitation.

Practical Example 1

Preparation of Plant Materials and Isolation of Procambium

Seed, needle, twig of the yew tree were collected. After collecting the materials, they were deposited in the solution of 100 mg/L of antioxidant, ascorbic acid (L-ascorbic acid, DUCHEFA, The Netherlands) immediately and transferred and preserved. They were surface sterilized by considering the morphology and physiological characteristics of the materials.

① Seed: After sterilizing the seeds with 70% ethanol for one minute, they were immersed in 1% Clorox solution for 48 hours and were washed 3 to 4 times with sterile water. Next, embryo was separated from the seed in the solution of 0.5% PVP (poly vinyl pyrrolidone, DUCHEFA, The Netherlands) and 50 mg/L of ascorbic acid (L-ascorbic acid, DUCHEFA, The Netherlands), and 70 mg/L of citric acid (DUCHEFA, The Netherlands) and cultured on the callus induction media.

② Needle and twig: After 24 hours of treatment with the solution containing 1% Benomyl (Dongbu Hannong Chemical, Korea)+1% Daconil (Dongbu Hannong Chemical, Korea)+1% Streptomycin sulphate (DUCHEFA, The Netherlands)+0.1% Cefotaxime sodium (DUCHEFA, The Netherlands), needles and twigs were rinsed with tap water for 30 seconds to remove the remaining chemical substances and phenolic compounds. After sterilizing them with 70% ethanol (DC Chemical, Korea) for one minute, 30% hydrogen peroxide (LG Chemical, Korea) for 15 minutes, 1% CLOROX solution for 15 minutes, 3% CLOROX solution for 5 minutes in order, they were washed 3 to 4 times with distilled water. To prevent the oxidation, both ends of the needle were cut in the solution of 0.5% PVP, 50 mg/L ascorbic acid and 70 mg/L citric acid and cultured on the callus induction media.

③ Procambium preparation from an apex of the twig: By holding the xylem which is the center region of an apex in the twig with the tweezers, phloem and cortex and epidermis tissues including the procambium were peeled off. This peeled tissue that contained procambium were laid on the media; procambium was allowed to touch the surface of the media.

Practical Example 2

Induction of Single Cell Clone from the Isolated Procambium

Figure 1:
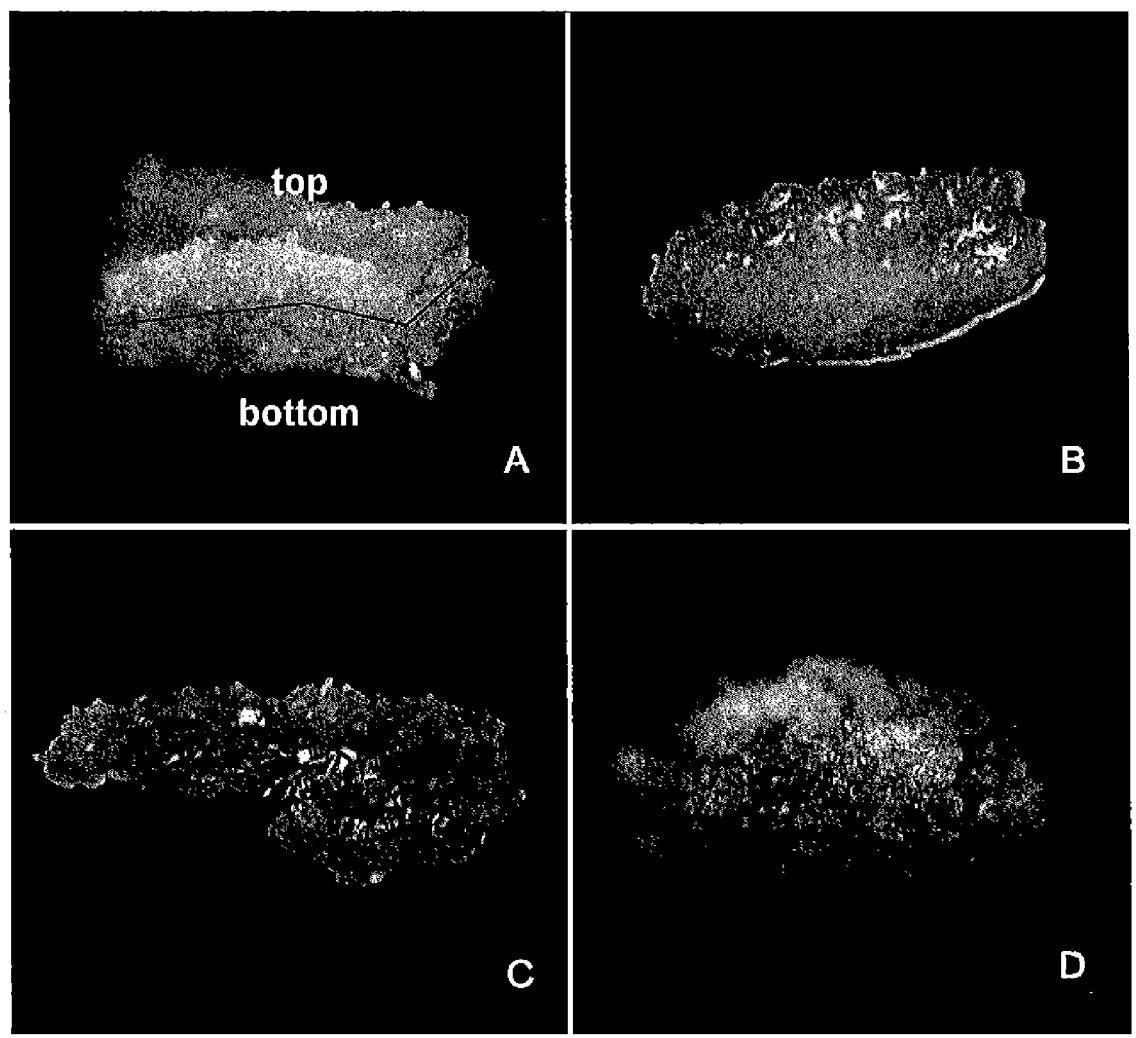
FIG. 1 is the part which was separated during the induction of single cell clone from the procambium (A: Macrography of twig after 30 days of cultivation—the procambium (bottom) is separated by callus cells derived from tissue consists of a primary phloem, cortex and epidermis; B: Single cell clone derived from procambium after 35 days of cultivation; C: Callus derived from tissue consists of a primary phloem, cortex and epidermis after 40 days of cultivation; D: Callus derived from embryo or needle after 50 days of cultivation).

After 4 to 7th day of the culture, cell division of the procambium was observed and on the 15$^{th}$ day of the culture, callus was beginning to form from the layer consisted of the phloem and cortex and epidermis that were the upper part of the procambium. On the 30$^{th}$ day of the culture, the procambium began to be separated from the upper layer tissue that contained the phloem and cortex and epidermis; after these two layers were completely separated naturally, they were cultured individually on different petri dishes (FIG. 1).

For the purpose of cell and callus induction, universally known media of the plant cell and tissue culture could be used: e.g. mB5 (modified Gamberg's B5 medium), MS (Murashige & Skoog medium), WPM (Lloyed & McCown), SM (schenk & Hildebrand medium), LP (Quoirin & Lepiovre). Application of all these media is possible. Various additives could be supplemented and components of the media could be reduced or eliminated as the need arises. Among them, the most appropriate media was mB5. The contents of mB5 are described in the following Table 1.

TABLE 1

Table 1. Cell line induction & maintenance medium in *Taxus* spp.

| | Composition | Contents (mg/L) |
|---|---|---|
| Inorganic salts | $KNO_3$ | 2500 |
| | $(NH_4)_2SO_4$ | 134 |
| | $MgSO_4 \cdot 7H_2O$ | 121.56 |
| | $MnSO_4 \cdot 4H_2O$ | 10 |
| | $ZnSO_4 \cdot 7H_2O$ | 2 |
| | $CuSO_4 \cdot 5H_2O$ | 0.025 |
| | $CaCl_2 \cdot 2H_2O$ | 113.23 |
| | KI | 0.75 |
| | $CoCl_2 \cdot 6H_2O$ | 0.025 |
| | $NaH_2PO_4 \cdot H_2O$ | 130.44 |
| | $H_3BO_3$ | 3 |
| | $Na_3MoO_4 \cdot 2H_2O$ | 0.25 |
| | FeNaEDTA | 36.7 |
| Vitamin | Myo-Inositol | 200 |
| | Thiamine-HCl | 20 |
| | Nicotinic acid | 2 |
| | Pyridoxine-HCl | 2 |
| | L-ascorbic acid | 50 |
| | Citric acid | 75 |
| Amino acid | L-aspartic acid | 133 |
| | L-arginine | 175 |
| | Glycine | 76 |
| | Proline | 115 |
| Hormone | a-Naphtalene acetic acid | 2 |
| Sucrose | | 10,000 |
| Activated charcoal | | 100 |
| Gelrite | | 2,000 |

The cultures were grown on the media that was supplemented with a plant growth regulator, auxin (1-3 mg/L) in the dark at 25±1° C.

Procambium was composed of homogeneous cells, so its cell division was uniform and proliferation occurred in the form of a plate. On the other hand, the tissue containing the phloem and cortex and epidermis proliferated in irregular form because there was a discrepancy of cell division due to the composition of many kinds of cells. There was a self-split of the layer in between the procambium and the tissue containing phloem and cortex and epidermis (FIG. 1). Procambium was homogeneous and the tissue containing phloem and cortex and epidermis was heterogeneous, so the self-split of the layer seemed to be the result of different division rate.

After 15$^{th}$ day of the culture, calli were formed on the explants of embryo and needle that are composed of heterogeneous cells by differentiation and these calli proliferated in irregular forms due to the different division rate of various cells just like the tissue that contained phloem and cortex and epidermis. (FIG. 1)

Practical Example 3

Establishment of Long Term Culture

Among the calli, white and friable parts that had good growth rate were subcultured onto the new media every 14 days. Growth rate of the embryo and needle-derived cultures was very unstable and it often showed the tendency of browning. On the contrary, growth rate of procambium-derived cultures was fast and there was no color change of the cultures. Therefore, it was possible to select the stable cells.

After six months of the culture, most of the embryo and needle-derived cultures had yellow or light brown color and aggregation formed. Procambium-derived cultures had white-yellow color and were maintained as single cells or small cell clusters. Growth rate of the cultures that turned brown and formed aggregation slowed down and the cultures died eventually because of the phenol chemical substance that they excreted.

Figure 2:
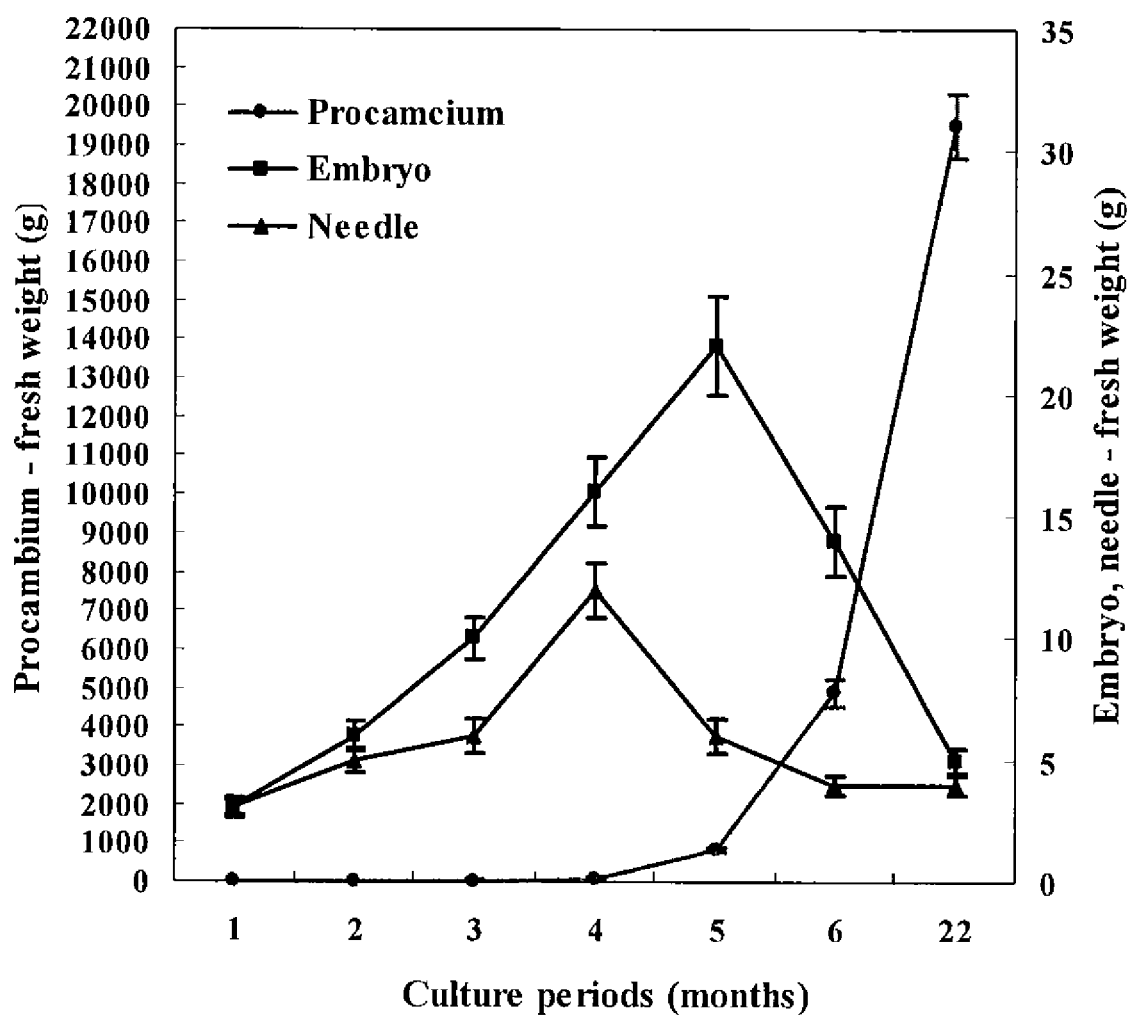
FIG. 2 is the growth rate expressed by the total biomass production of three different cell cultures derived from procambium, embryo and needle of *T. cuspidate* in 22 months (The subculture interval ranged between 14 days).
Figure 3:
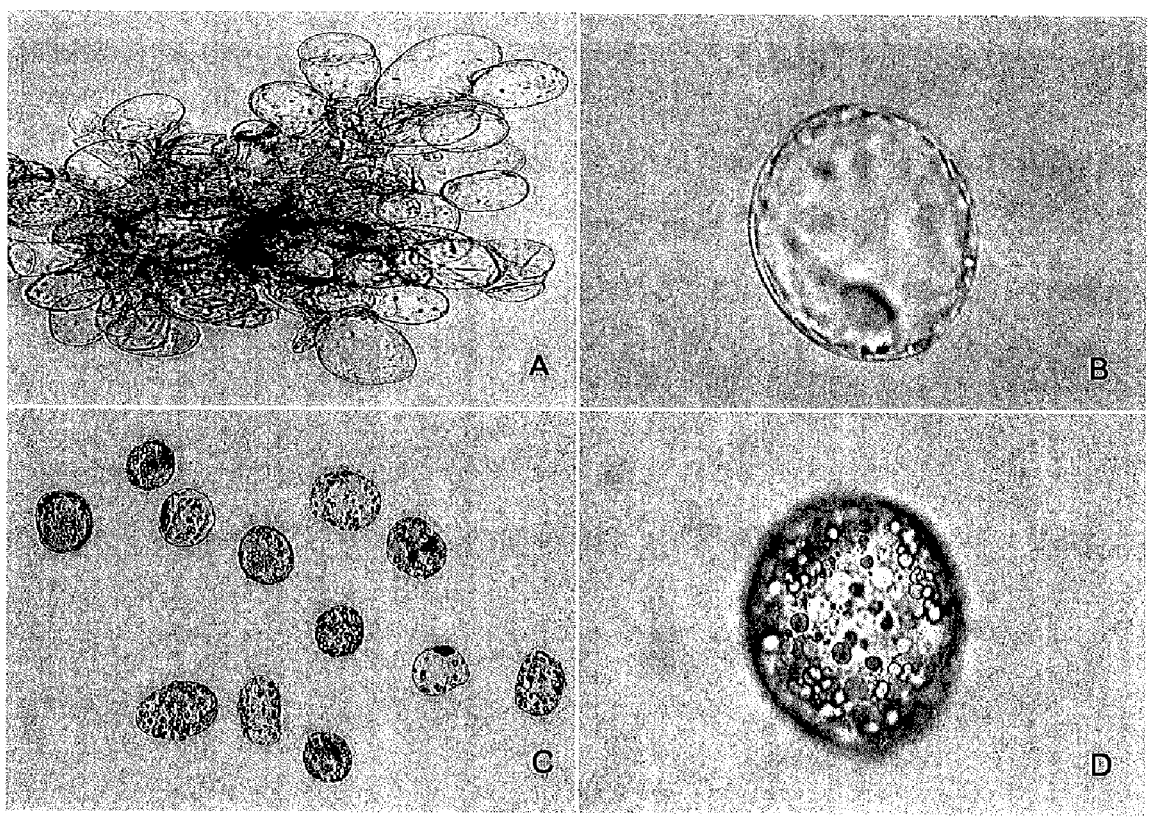
FIG. 3 is the image of cell aggregation of the cultures derived from two different tissues (A & B: embryo or needle; C & D: procambium) of *T. cuspidata* (A: Large cell aggregates, size higher than $1.5 \times 10^2$ μm; C: single cell population; D: cell presenting a high density of vacuole.).

According to this inventor, maintenance and mass proliferation of the embryo and needle-derived cultures was difficult after 6 months, but procambium-derived cultures were maintained stably for more than 20 months of the long term culture without any variation in the rate of cell growth, growth pattern and aggregation level (FIG. 2). In other words, variability appeared in growth pattern, depending on the homogeneity and heterogeneity of the initial plant materials.

Practical Example 4

Establishment of Cell Suspension Culture

The embryo and needle-derived and procambium-derived cultures were cultured individually in the flask containing the liquid media (Table 2).

TABLE 2

Table 2. Suspension medium in *Taxus* spp.

|  | Composition | Contents (mg/L) |
|---|---|---|
| Inorganic salts | Ca(NO$_3$)$_2$ | 471.26 |
|  | NH$_4$NO$_3$ | 400 |
|  | MgSO$_4$•7H$_2$O | 180.54 |
|  | MnSO$_4$•4H$_2$O | 22.3 |
|  | ZnSO$_4$•7H$_2$O | 8.6 |
|  | CuSO$_4$•5H$_2$O | 0.25 |
|  | CaCl$_3$•2H$_2$O | 72.5 |
|  | K$_2$SO$_4$ | 900 |
|  | Na$_2$MoO$_4$•2H$_2$O | 0.25 |
|  | H$_3$BO$_3$ | 6.2 |
|  | KH$_2$PO$_4$ | 170 |
|  | FeNaEDTA | 36.7 |
| Vitamin | Myo-Inositol | 200 |
|  | Thiamine-HCl | 20 |
|  | Nicotinic acid | 2 |
|  | Pyridoxine-HCl | 2 |
|  | L-ascorbic acid | 50 |
|  | Citric acid | 75 |
| Amino acid | L-aspartic acid | 133 |
|  | L-arginine | 175 |
|  | Glycine | 76 |
|  | Proline | 115 |
| Hormone | a-Naphtalene acetic acid | 2 |
| Sucrose |  | 30,000 |

They were cultured on the 100 rpm rotating shaker in the dark at 25±1° C. With the two weeks of subculture interval, cultures were allowed to maintain high vitality continuously as exponential growth phase.

Aggregation level which is the main cause of the variation of cell productivity was measured. Cell aggregate quantification was measured with the biological microscope (CX31, Olympus, Japan). The result of the experiment described above is on Table 3.

TABLE 3

Type of cell aggregates of *Taxus* long-term cultures

| Large cell aggregates | Moderate cell aggregates | Small cell aggregates | Single cell population | Explant source |
|---|---|---|---|---|
| 60 ± 3.2% | 30 ± 3.3% | 7 ± 0.6% | 3 ± 0.9% | embryo, needle |
| 0 | 0 | 7.4 ± 0.8% | 92.6 ± 0.8% | procambium |

Large cell aggregates, size higher than 1.5 × 10$^3$ μm;
Moderate cell aggregates, 1 × 10$^3$ μm;
Small cell aggregates, 4 × 10$^2$ μm < size < 1 × 10$^3$ μm In case of the suspension of the embryo and needle-derived cultures, about 60% had cell aggregation size more than 1.5 mm but in the suspension of procambium-derived cultures, 92.6% of the cells were cultured as single cells.

Practical Example 5

Scale Up

Embryo and needle-derived and procambium-derived cultures were cultured in 3 L airlift bioreactor (Sung-Won SciTech, Korea) in the dark at 25±1 C°.

In case of the embryo and needle-derived cultures, there was a great variability in the size and shape of the cells compared to the flask culture. Diameter of the cell aggregation was enlarged up to 2-3 mm, which inhibited the flow inside of the bioreactor and developed unmixed region in the bioreactor. Growth ring formed by the cells adhering to the internal wall of the bioreactor. Cells in the center of the growth ring died after 20 days because the media was not supplied efficiently. Eventually dead cells excreted toxic substances and these substances lowered the vitality of all cells in the bioreactor. On the opposite, less aggregation of procambium-derived cultures caused smooth air circulation in the bioreactor; hence it was possible to diminish the amount of air supply from 200 ml to 150 ml per minute and the amount of developed bubble on the surface of the media was greatly reduced.

Doubling time of the embryo and needle-derived cultures in the flask was 12 days but it was lengthened to 21 days in the bioreactor. It was because of the growth ring formation and rapid decrease of cell viability due to sensitiveness to shear by cell aggregation and rigid cell wall. Doubling time of procambium-derived cultures was 4 to 5 days and there was no difference in the flask and the bioreactor, rather it was shortened in the bioreactor (Table 4). Procambium-derived cultures formed very small growth ring in the bioreactor and the growth ring was dissolved easily by agitating the media with a simple stimulus. Moreover, there was no decrease in cell viability due to less sensitivity to shear by less cell aggregation and multiple vacuoles.

TABLE 4

Relationship between doubling time patterns and explants source in *T. cuspidata* cell cultures in flask and bioreactor

|  | Doubling time (day) | |
|---|---|---|
| Explant source | flask | bioreactor |
| embryo | 11.5 ± 1.3 | 21 ± 2.6 |
| needle | 12 ± 2 | 21 ± 2 |
| procambium | 5 ± 0.2 | 4 ± 0.1 |

Practical Example 6

Elicitor

Figure 4:
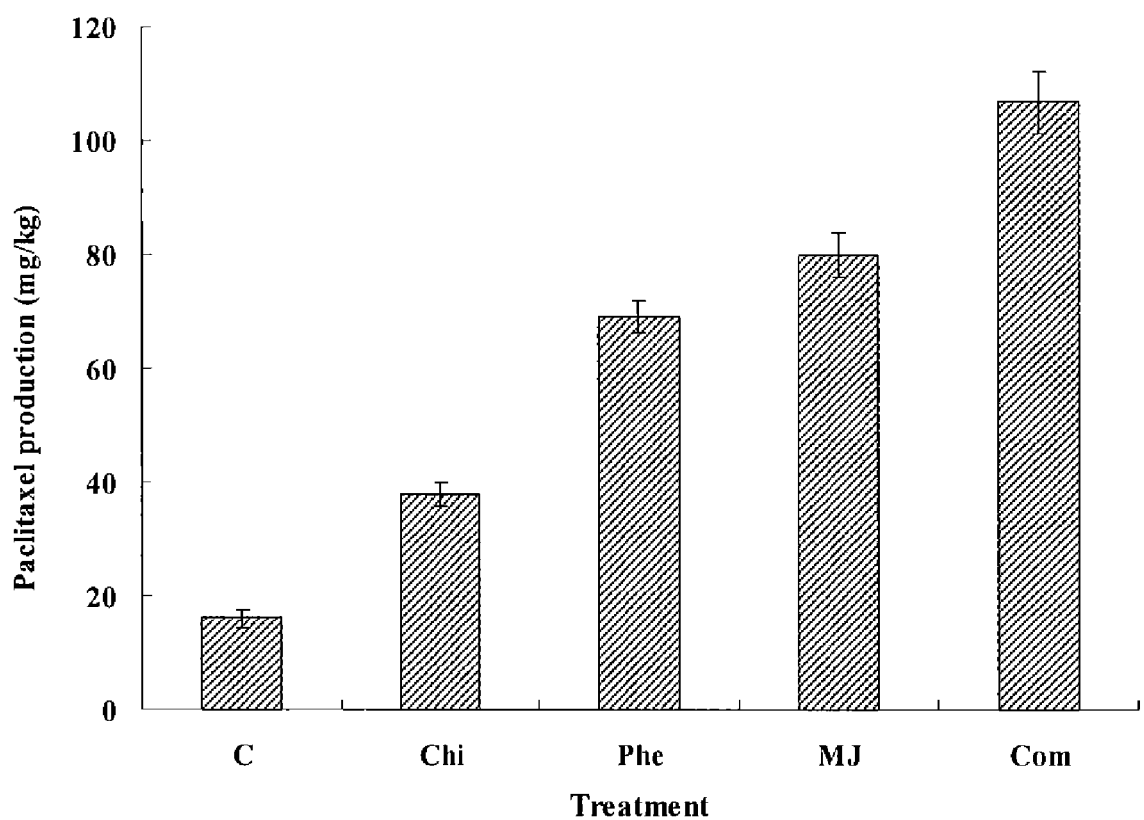
FIG. 4 is the effects of elicitors and their combinations on paclitaxel production in *T. cuspidata* (single cell clone from procambium) suspension cultures (Conditioning factors were incorporated to zero-day cultures. Symbols: C, control; Chi, 50 mg/L Chitosan; Phe, 0.1 mM Phenylalanine; MJ, 100 μM Methyl jasmonate; Com (Combined-elicited cultures), the combination of 50 mg/L Chitosan, 0.1 mM Phenylalanine and 100 μM Methyl jasmonate.).

Elicitor controls molecular signal in plant cells and is widely used for the increase of secondary metabolite productivity. After the treatment of methyl jasmonate as an elicitor and 10 other kinds of elicitors, we observed that methyl jasmonate had positive effect on the paclitaxel production. It was possible to obtain relatively high metabolites productivity through the combination of methyl jasmonate and other elicitors. Especially, paclitaxel production was very effective with the treatments of methyl jasmonate, chitosan and phenylanine (FIG. 4).

Practical Example 7

Conditioning Factors

Plant derived secondary metabolites are produced when the cells are growing or when the cells stopped growing. Therefore, two stage cultures are suitable for the production of metabolites like paclitaxel whose cell growth stage and metabolite production stage are separated. In the first stage, cells were proliferated in a large scale by optimizing the cell growth and in the second stage, the culture condition was changed for the optimization of metabolites production.

Cell lines with high secondary metabolites productivity grow slower and die faster than the cell lines with low productivity. Therefore, mass proliferation is difficult and mass production of the metabolites is impossible.

Figure 5:
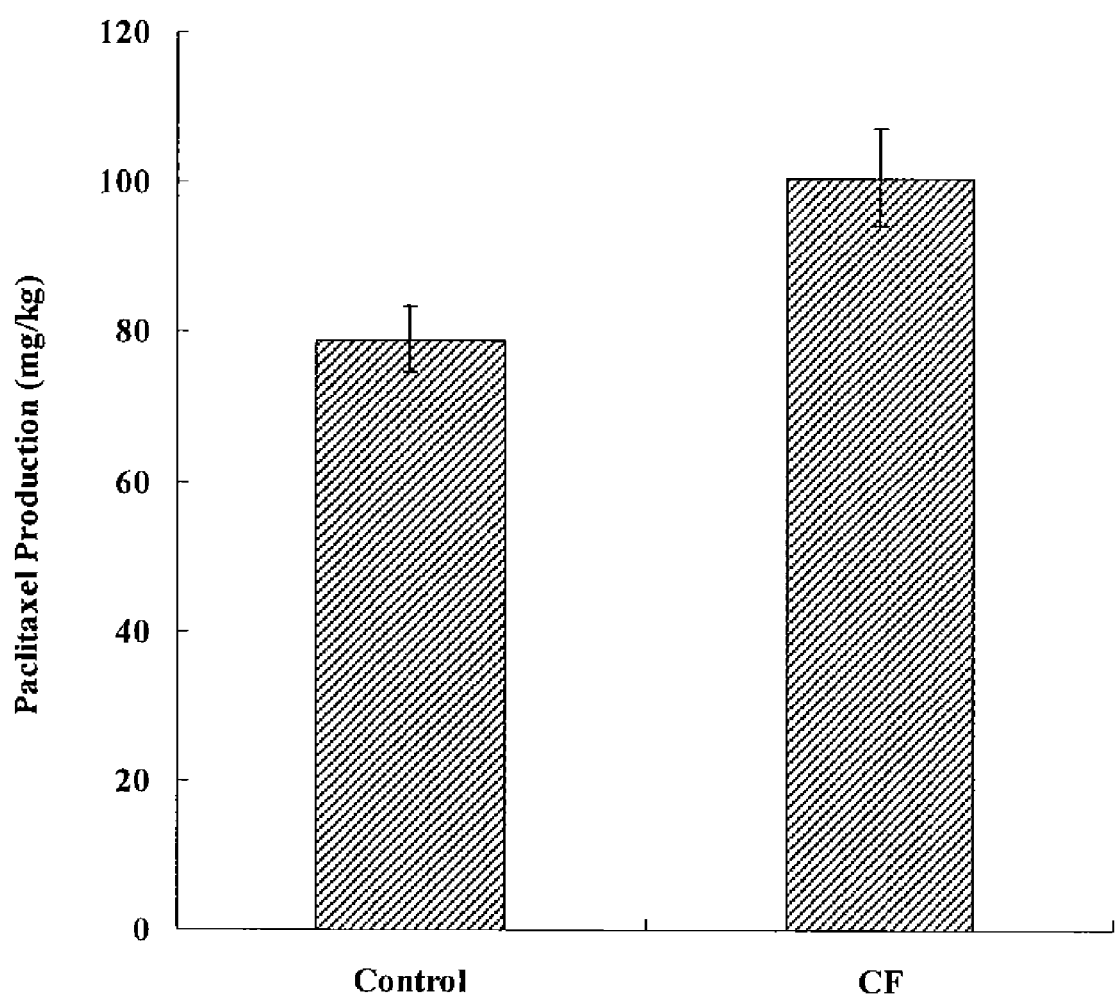
FIG. 5 is the effect of conditioning factors on paclitaxel production in *T. cuspidata* (single cell clone from procambium) suspension cultures (Elicitors (50 mg/L Chitosan, 0.1 mM Phenylalanine and 100 μM Methyl jasmonate) were incorporated to 14-day-old cultures. Symbol: CF, conditioning factors.).

In this invention, cell lines with the ability of low proliferation and high production were not used for the proliferation in large scale, rather they were used as the helper cells that have the conditioning factors for the production of secondary metabolites. We observed the paclitaxel production after adding the helper cells. The results are summarized in FIG. 5.

Practical Example 8

Perfusion Culture

On the day 14 of culture, elicitor was treated to the embryo and needle-derived and procambium-derived cultures. From the point of elicitation, spent media was retrieved in an aseptic condition with pipette on every 5 days and was supplied with the same amount of new media simultaneously. The production of paclitaxel in the cell and the media were observed after 45 days of the long term culture. The result was summarized in Table 5.

Depending on the cell lines, paclitaxel release of the cell to the media was different. Releasing ability of procambium-derived cultures was superior to the cultures of the preceding techniques. The procambium-derived single cell clone has an ability of releasing about 404~1077 times more paclitaxel than the cell lines derived from embryo and needle (in medium of Table 5). Moreover, application of perfusion culture facilitated the release of secondary metabolites to the media. Improvement in the extracellular release of secondary metabolites through procambium-derived single cell clone by exchanging the media periodically had great importance because it allowed continuous recycle of the biomass and simple purification.

In other words, periodical exchange of the media in the procambium-derived single cell clone culture can be considered as a stable method of producing valuable metabolites in the long term culture, because it prevents feedback inhibition of accumulated metabolites in the cell, degradation and conversion of the metabolites in the media.

Practical Example 9

Cryopreservation

On the $6^{th}$ or $7^{th}$ day of the culture, suspension cells were pre-cultured in the media containing 0.16M of manitol for 3 days at the room temperature and then maintained at 4° C. for 3 hours. Cells were harvested and placed into 4 ml cryovial which had the media containing 40% ethylene glycol (Sigma, USA) and 30% sorbitol (DUCHEFA, The Netherlands) and cultured for 3 minutes at 4° C.

Suspension cells that were treated with cryopreservatives were frozen after the cells were soaked in the liquid nitrogen. For thawing, cultured cells in the liquid nitrogen for more than 10 minutes were thawed in the 40° C. water bath for 1-2 minutes. For the re-growth of the cells, cryopreserved cells were transferred onto the semi-solid growth media (Table 1) containing 0.5 M sorbitol and alleviated at the room temperature for 30 minutes. Cells were cultured on the semi-solid growth media containing 0.1M sorbitol for 24 hours. And then, the cells were cultured on the semi-solid growth media without sorbitol for 24 hours, twice. Cell viability was evaluated.

Practical Example 10

Analysis of Paclitaxel Content

After separating the cells from the media of the recovered samples, paclitaxel contents were analyzed. Cell mass was measured after drying the cells completely with vacuum desicator (Sam Shin Glass, Korea). About 100 mg (dry weight) of the cells were mixed with 4 ml solution (1:1 v/v) of methanol (Sigma, USA) and methylchloride (Sigma, USA) and were extracted by ultrasonic cleaner (Branson, USA) for 3 times in

TABLE 5

Paclitaxel production and release of *T. cuspidata* cells in various explant sources and processes.

| Materials & processes | Taxol yield (mg/kg) | | | Taxol release(%) |
|---|---|---|---|---|
| | In cell | In medium | Total (days) | |
| embryo | 12.97 ± 1.16 | 0.03 ± 0.01 | 13 ± 1.17 (28) | 0.2 ± 0.1 |
| needle | 10.92 ± 1.6 | 0.08 ± 0.01 | 11 ± 1.6 (28) | 0.7 ± 0.1 |
| procambium | 86.4 ± 6.7 | 32.3 ± 7.6 | 118.7 ± 3.3 (28) | 27.1 ± 6.1 |
| procambium | 0 | 0 | 0 (45) | — |
| Procambium perfusion culture | 65.5 ± 4.1 | 171.8 ± 11.1 | 237.3 ± 7 (45) | 72.3 ± 2.5 | one hour interval at the room temperature. Cells were fully dried and extracted several times by using 4 ml of methylchloride. Separated organic solvent layer was vacuum dried and the remaining was dissolved in 1 ml of methanol. Dissolved extract was agitated equally by ultrasonic cleaner. Then, after centrifugation, the pellet was removed (8,000 g×5 min).

Media (1-5 ml) that was separated from the cell was combined with the same volume of methylchloride and was extracted 3 times after full agitations. After organic solvent was vacuumed and dried completely, it was dissolved in 0.5 ml of methanol again.

HPLC (High Performance Liquid Chromatography, Shiseido, Japan) was used for the analysis of the content and Sigma products were used for paclitaxel standard substances. Capcell pak (C18, MGII, 5 um, 3.0 mm×250 mm, Shiseido, Japan) was maintained to 40° C. by using the oven, and water and acetonitril (Burdick & Jackson, USA) (50:50, v/v) were combined for the mobile phase and dropped regularly with the speed of 0.5 ml/min. UV-VIS detector (227 nm, Shiseido, Japan) was used.

INDUSTRIAL APPLICABILITY

In this invention, acquiring single cell clone, a primary meristem which has the meristematic continuity without dedifferentiation, by separating procambium purely from an apex of the twig resulted in higher productivity due to shorter doubling time than the cell lines of preceding techniques. It also allowed stable productivity due to less change in the cell growth and growth pattern during the long term culture and scale up was possible because of less aggregation and multiple vacuoles of the cell lines. This cell lines allowed recovery after cryopreservation without any genetic variation.

REFERENCES

1. Gamborg, O. L., Miller, R. A., Ojima, K. 1968. Nutrient requirement of suspension cultures of soybean root cells. *Exp. Cell. Res.*, 50: 151
2. Hirasuna T. J., Pestchanker L. J., Srinivasan V., Shuler M. L. (1996) Taxol production in suspension cultures of *Taxus baccata*. *Plant cell tissue and organ culture*. 44:95-102
3. Jouira H. B., Hassairi A., Bigot C., Dorion N. (1998) Adventitious shoot production from strips of stem in the Dutch elm hybrid 'Commelin': plantlet regeneration and neomycin sensitivity. *Plant cell Tissue and Organ Culture*. 53:153-160
4. Kim M. H., Chun S. H., Kim D. I. (2000) Growth promotion of *Taxus brevifolia* cell suspension culture using conditioned medium. *Biotechnol bioprocess eng*. 5:350-354
5. Lloyd G. and McCown B. (1980) Commercially-feasible micropropagation of mountain laurel, kalmia latifolia by use of shoot-tip culture. *Plant Prop. Proc.* 30:421
6. Muraghige T. and Skoog F. (1962) A revised medium for rapid growth and bioassays with tobacco culture. *Physiol Plant* 15: 473-497
7. Naill M. C., Roberts S. C. (2004) Preparation of single cells from aggregated *Taxus* suspension cultures for population analysis. Published online 10 May 2004 in wiley interscience.
8. Quoirin M., Lepoivre P. (1977) Acta. Hart. 78: 437
9. Schenk R. U., Hildebrandt A. C (1972) Medium and techniques for induction and growth of monocotyledonous and dicotyledonous plant cell culture. *Can. J. Bot.* 50: 199
10. Wang C., Wu J., Mei X. (2001) Enhanced taxol production and release in *Taxus chininsis* cell suspension cultures with selectid organic solvents and sucrose feeding. *Biotechnol. Prog.* 17:89-94
11. Wang C., Wu J., Mei X. (2001) Enhancement of taxol production and excretion in *Taxus chininsis* cell culture by fungal elicitation and medium renewal. *Appl Microbiol Biotechnol.* 55:404-410
12. Wickremesinhe E. R. M., Arteca R. N. (1994) *Taxus* cell suspension cultures: optimizing growth and production of taxol. *J. Plant Physiol.* 144:183-188
13. Wu J., Lin L. (2003) Enhancement of taxol production and release in *Taxus chinensis* cell cultures by ultrasound, methyl jasmonate and in situ solvent extraction. *Appl Microbiol Biotechnol.* 62:151-155
14. Yokoi H., J. Koga, K. Yamamura and Y. Seike, (1993) High density cultivation of plant cells in a new aeration-Agitation type fermentor. 75:48-52
15. Zhang C. H., Mei X. G., Liu L., Yu L. J. (2000) Enhanced paclitaxel production induced by the combination of elicitors in cell suspension cultures of *Taxus chinensis*. *Biotechnology Letters*. 22:1561-1564
16. Zhong J. J. (2002) Plant cell culture for production of paclitaxel and other taxanes. *J. bioscience and bioengineering.* 94:591-599

The invention claimed is:

1. An isolated population of cells from a plant, wherein the cells of the isolated population are characterized in that they (i) are derived from procambium of the plant, (ii) are innately undifferentiated, (iii) are homogeneous, and (iv) comprise the following characteristics:
   (a) including a greater number of single cells or including smaller-sized cell aggregates in suspension culture than cells derived from dedifferentiated callus of the plant;
   (b) having multiple vacuoles morphologically;
   (c) being capable of growing faster and longer than cells derived from dedifferentiated callus of the plant; and
   (d) having lower sensitivity to shear stress in a bioreactor than cells derived from dedifferentiated callus of the plant.

2. The isolated population of cells according to claim 1, wherein the plant is the genus *Taxus*.

3. The isolated population of cells according to claim 2, wherein the cells are capable of releasing paclitaxel 404-1077 times more than cells derived from dedifferentiated callus of the plant.

4. A method for producing a biologically active substance or substances, the method comprising the steps of:
   (a) producing the active substance or substances by culturing in a medium the isolated population of cells of claim 1; and
   (b) collecting said active substance or substances.

5. The method according to claim 4, wherein in the step (a), a predetermined amount of the medium that has been used to culture the cells is removed and a predetermined amount of a new medium is introduced.

6. The method according to claim 4, wherein the plant is the genus *Taxus* and the active substance is paclitaxel.

7. The method according to claim 6, wherein the medium includes at least one component selected from the group consisting of methyl jasmonate, phenylalanine, and chitosan.

8. A method for preserving a plant cell line, the method comprising cryopreserving the isolated population of cells of claim 1.

* * * * *